(12) United States Patent
Stefan

(10) Patent No.: US 9,494,417 B2
(45) Date of Patent: Nov. 15, 2016

(54) METHOD FOR DETERMINING A SHAPE CORRECTION VALUE F FOR LABORATORY LIQUID-ANALYSIS CUVETTES

(75) Inventor: Frank Stefan, Berlin (DE)

(73) Assignee: HACH LANGE GMBH, Berlin (DE)

( * ) Notice: Subject to any disclaimer, the term of this patent is extended or adjusted under 35 U.S.C. 154(b) by 0 days.

(21) Appl. No.: 13/978,143

(22) PCT Filed: Dec. 19, 2011

(86) PCT No.: PCT/EP2011/073239
§ 371 (c)(1),
(2), (4) Date: Sep. 5, 2013

(87) PCT Pub. No.: WO2012/093028
PCT Pub. Date: Jul. 12, 2012

(65) Prior Publication Data
US 2013/0337574 A1    Dec. 19, 2013

(30) Foreign Application Priority Data
Jan. 4, 2011 (EP) .................... 11150065

(51) Int. Cl.
*G01B 11/24* (2006.01)
*G01B 11/08* (2006.01)
(Continued)

(52) U.S. Cl.
CPC .............. *G01B 11/24* (2013.01); *G01B 11/08* (2013.01); *G01B 11/12* (2013.01); *G01N 21/274* (2013.01); *G01N 21/5911* (2013.01); *G01N 35/00732* (2013.01); *B01L 3/5082* (2013.01); *B01L 2200/143* (2013.01); *B01L 2300/021* (2013.01); *B01L 2300/042* (2013.01); *B01L 2300/0654* (2013.01); *B01L 2300/0832* (2013.01); *B01L 2300/0858* (2013.01); *G01N 21/03* (2013.01); *G01N 21/251* (2013.01); *G01N 2201/121* (2013.01)

(58) Field of Classification Search
CPC .................... G01N 21/274; G01N 2035/00752
USPC ........................................................ 436/164
See application file for complete search history.

(56) References Cited

U.S. PATENT DOCUMENTS 4,953,973 A * 9/1990 Levine et al. .................. 356/32
4,953,975 A   9/1990 Levine et al.
(Continued)

FOREIGN PATENT DOCUMENTS

DE    39 21 393 A1    1/1991
DE    41 09 118 A1    9/1992
(Continued)

*Primary Examiner* — Lyle Alexander
*Assistant Examiner* — Emily Berkeley
(74) *Attorney, Agent, or Firm* — Norman B. Thot

(57) ABSTRACT

A method for determining a shape correction value F for a laboratory liquid-analysis cuvette comprising a cuvette body with a circular cross-section for a photometric liquid analysis includes optically measuring an inside diameter $d_i$ or an outside diameter $d_o$ of the cuvette body to obtain a measured cuvette body diameter $d_i;d_o$. A shape correction value F is calculated from the measured cuvette body diameter $d_i;d_o$. The shape correction value F for the cuvette body is stored.

10 Claims, 3 Drawing Sheets

(51) Int. Cl.
  *G01B 11/12*   (2006.01)
  *G01N 21/27*   (2006.01)
  *G01N 21/59*   (2006.01)
  *G01N 35/00*   (2006.01)
  *G01N 21/03*   (2006.01)
  *G01N 21/25*   (2006.01)
  *B01L 3/00*   (2006.01)

(56) References Cited

U.S. PATENT DOCUMENTS

| | | | | |
|---|---|---|---|---|
| 5,386,287 A | * | 1/1995 | Berssen et al. | 356/326 |
| 5,568,262 A | * | 10/1996 | LaChapelle et al. | 356/627 |
| 6,980,285 B1 | | 12/2005 | Hansen | |
| 2004/0086173 A1 | * | 5/2004 | Itoh | G06K 9/00 |
| | | | | 382/152 |
| 2005/0071110 A1 | * | 3/2005 | Davis | 702/123 |

FOREIGN PATENT DOCUMENTS

| | | |
|---|---|---|
| JP | 55-69027 A | 5/1980 |
| JP | 60-231171 A | 11/1985 |

\* cited by examiner

METHOD FOR DETERMINING A SHAPE CORRECTION VALUE F FOR LABORATORY LIQUID-ANALYSIS CUVETTES

CROSS REFERENCE TO PRIOR APPLICATIONS

This application is a U.S. National Phase application under 35 U.S.C. §371 of International Application No. PCT/EP2011/073239, filed on Dec. 19, 2011 and which claims benefit to European Patent Application No. 11150065.8, filed on Jan. 4, 2011. The International Application was published in German on Jul. 12, 2012 as WO 2012/093028 A1 under PCT Article 21(2).

FIELD

The present invention relates to a method for determining a shape correction value F for laboratory liquid-analysis cuvettes for photometric laboratory analyzers.

BACKGROUND

In the field of laboratory analysis, so-called cuvette tests have become standard, among others, which tests consist of cuvettes filled with a reagent, the cuvettes being placed into a laboratory analyzer for a quantitative analysis after the liquid sample has been filled in. The reagent, already filled into the cuvette by the manufacturer, reacts in a color changing manner with the analyte of the water or waste water sample to be analyzed. This color change is determined quantitatively in the laboratory analyzer by means of its photometer. For this purpose, the cuvette is photometered in the radial direction as described in DE 41 09 118 A1.

SUMMARY

An aspect of the present invention is to improve the accuracy of the measuring results of cuvette tests.

In an embodiment, the present invention provides a method for determining a shape correction value F for a laboratory liquid-analysis cuvette comprising a cuvette body with a circular cross-section for a photometric liquid analysis which includes optically measuring an inside diameter $d_1$ or an outside diameter $d_0$ of the cuvette body (12) to obtain a measured cuvette body diameter $d_1;d_0$. A shape correction value F is calculated from the measured cuvette body diameter $d_1;d_0$. The shape correction value F for the cuvette body is stored.

BRIEF DESCRIPTION OF THE DRAWINGS

The present invention is described in greater detail below on the basis of embodiments and of the drawings in which.

DETAILED DESCRIPTION

Figure 1:
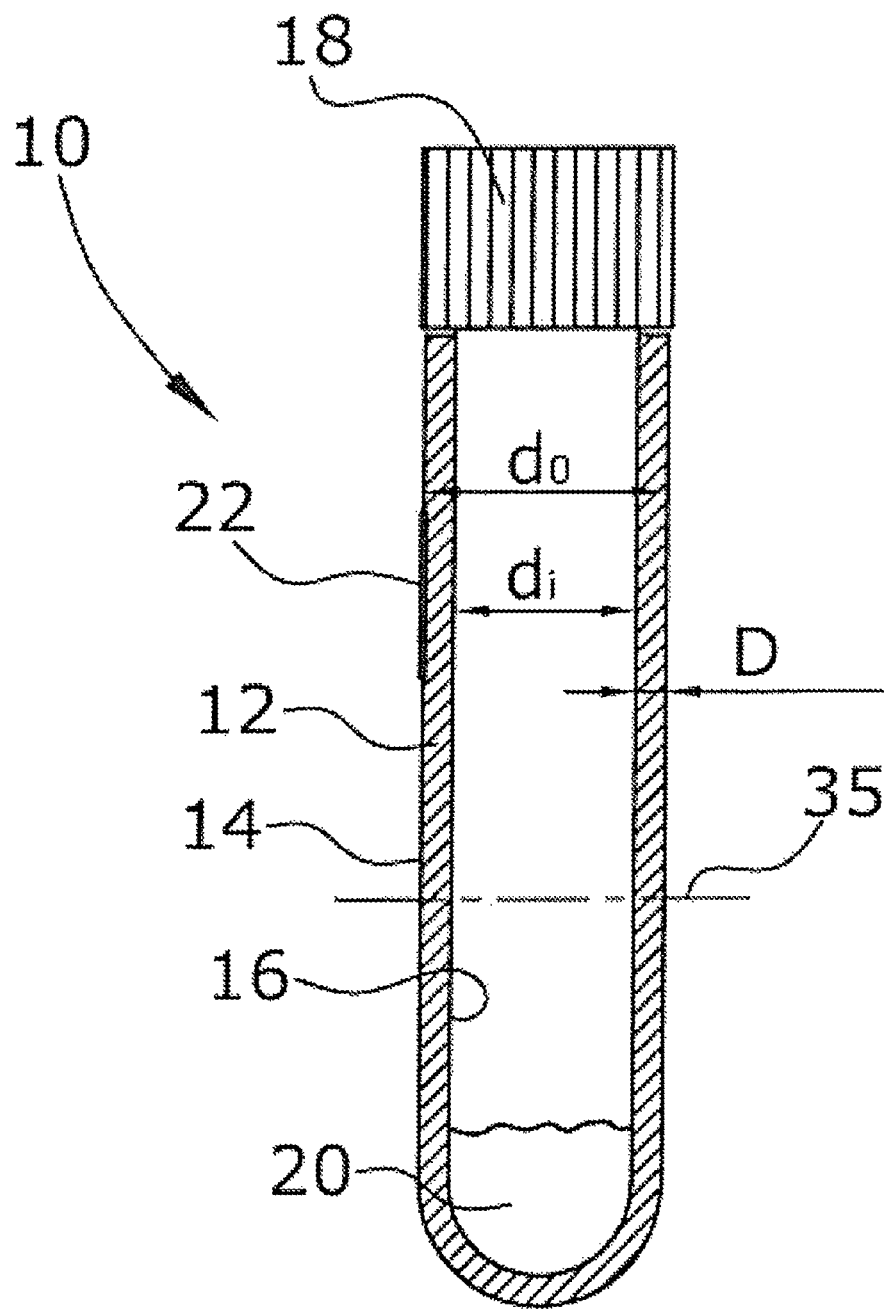
FIG. 1 shows a longitudinal section of a cuvette.

The present invention for determining a shape correction value F for laboratory liquid-analysis cuvettes having a cuvette body of circular cross section first provides an exact optical measurement or a measuring of the inner or the outer diameter of the cuvette body. From the measured inner or outer diameter of the cuvette body, a shape correction value F is determined that is stored at or on the cuvette body of each cuvette.

During the manufacture of the cuvettes, variations in the diameter of the cuvette bodies occur that are within a single-digit percentage range. Cuvettes that differ substantially from a set value can of course be rejected. In the interest of an economic manufacturing of cuvettes, a diameter variation of 1 to 2% must, however, be accepted. The length of the photometric measuring path extending in the radial direction through the cuvette thereby also varies by 1 to 2% inside the cuvette, whereby, also the characteristic of the analyte concentration relative to the measured absorbance is influenced, which is determined transmissively by means of a photometer of the laboratory analyzer.

The exact determination of the individual diameter of each cuvette allows an exact determination of the measuring path inside the cuvette. The inner diameter of the cuvette body can, for example, be measured for this purpose, however, it is also possible, assuming a rather constant wall thickness of the cuvette body, to make an exact conclusion on the length of the measuring path inside cuvette body also from the outer diameter of the cuvette body. The shape correction factor F therefore provides the analyzer with a value that correlates with the exact length of the measuring path inside the specific cuvette. The correction factor F is read out or from the cuvette in the analyzer.

The absorbance measured by the photometer can be corrected correspondingly using the correction factor F. As tests have shown, the accuracy of the quantitative determination of the analyte in the liquid sample is increased by about five times, i.e., the error is reduced to 20% of the error without correction using a shape correction value F. It is also possible in this manner to reduce the rejects in cuvette production since the requirements on the dimensional stability of the cuvettes produced can be reduced. The average manufacturing costs for the cuvettes are thereby reduced.

The shape correction value F can, for example, be stored in a two-dimensional barcode fixed on the cuvette body in a manner visible from outside. A barcode fixed on the cuvette is a simple and economic means for assigning the shape correction value F to the cuvette in an immediate, assignment error-free and permanent manner. The barcode can be read, for example, by a corresponding one- or two-dimensional barcode reader of the analyzer. The barcode reader may, for example, be arranged in the cuvette chamber of the analyzer into which the cuvette is inserted for photometry.

In an embodiment of the present invention, the diameter of the cuvette body is measured several times along the entire cuvette circumference. The shape correction value F is determined from all diameter values, for example, the arithmetic mean of the diameter values. A mean shape correction value F is determined in this manner. The cuvette bodies are cylindrical, i.e., circular in cross section. A defined rotational position of the cuvette in the analyzer cannot thus be provided. Analyzers are further used that comprise a cuvette turning device which turns the cuvette about its longitudinal axis during photometry so as to photometer the cuvette in a plurality of rotational positions. By determining and using a mean shape correction value F, the average accuracy of the measuring results is increased.

In an embodiment of the present invention, after the inner or outer diameter of the cuvette body has been measured, the cuvette is filled with a reagent reacting in a color changing manner with the analyte of the liquid sample to be determined. The cuvette is thereafter closed with a transport closure, for example, a screw cap. The transport closure is only opened by the end user to fill in the sample. After the water sample has been filled in, the cuvette can again be closed with the transport closure to enable a mixing of the water sample with the reagent in the cuvette by shaking.

The optical measuring or determination of the cuvette body diameter can, for example, be performed by means of a digital measuring camera. Given a sufficient resolution of the measuring camera, the inner and/or the outer diameter can be determined based on a single photo. The cuvette production process is affected thereby only slightly.

An embodiment of the method of the present invention provides, prior to calculating the shape correction value F, measuring both the outer and the inner diameter of the cuvette body, with the shape correction value F being determined from both the measured inner diameter and the measured outer diameter. Not only a single diameter value (i.e., either the outer or the inner diameter) is thereby determined, but both the outer diameter value and the inner diameter value are determined. It is also possible to determine the wall thickness of the cuvette body in this manner. This is in particular important when the photometry is performed in the UV range since the glass materials typically used for cuvette bodies absorb UV radiation to a relatively high degree. By measuring both the outer and the inner diameter and due the determination of the cuvette wall thickness enabled thereby, it is even possible to include the cuvette wall thickness, which may even vary along the circumference, in the shape correction factor F. The average accuracy of the measuring values generated from the photometry measuring signals is increased in this manner.

A detailed description of the present method with reference to the drawings is hereinafter provided.

FIG. 1 shows a cuvette 10 containing a solid or liquid reagent 20 and closed with a transport closure 18. The cuvette 10 is formed by a cuvette body 12 of glass. The reagent 20 may be solid or liquid. The cuvette body 12 has an outer side 14 and an inner side 16 and is substantially cylindrical, i.e., circular in cross section. The cuvette body 12 has an outer diameter $d_O$ and an inner diameter $d_I$. A two-dimensional barcode 22 is adhered to the outer side of the cuvette body 12.

Figure 2:
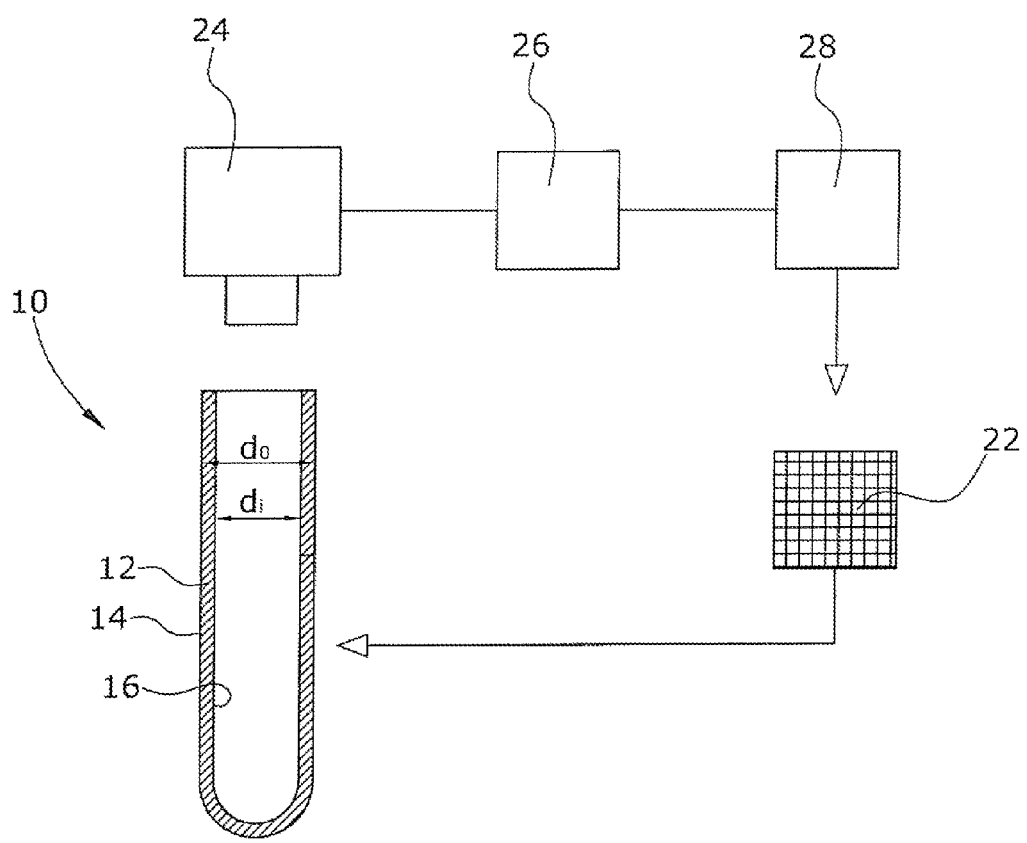
FIG. 2 shows an arrangement for measuring the inner and/or outer diameter of the cuvette body of the cuvette shown in FIG. 1.
Figure 3:
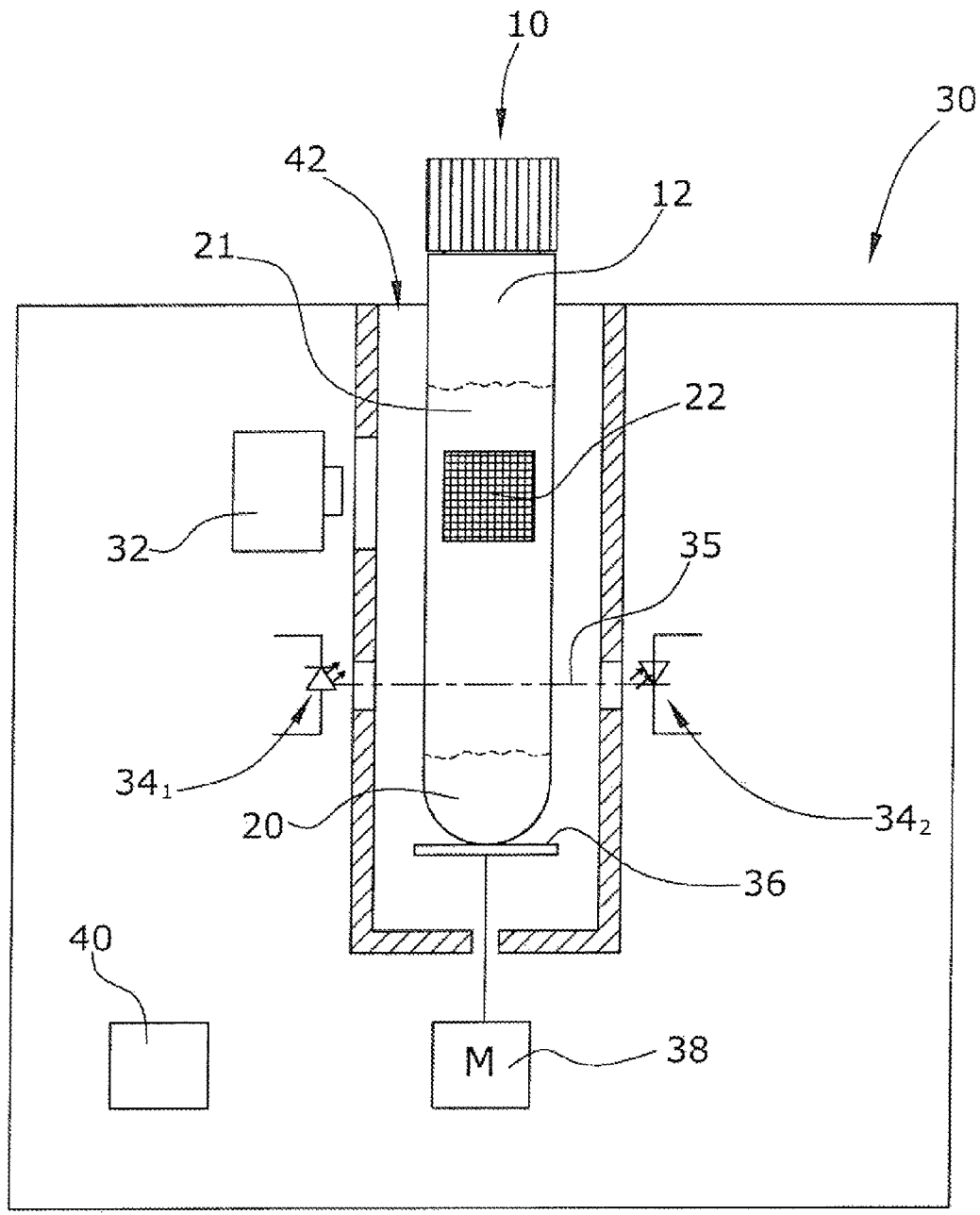
FIG. 3 shows an analyzer with a cuvette inserted therein.

The method of the present invention will be described hereinafter with reference to the FIGS. 2 and 3. First, the cuvette body 12 is measured optically using a digital measuring camera 24. For this purpose, the measuring camera 24 is, for example, oriented in axial alignment with the axis of the cuvette body 12 so that the measuring camera 24 is directed axially at the opening of the cuvette body 12. The measuring camera 24 takes a picture of the opening side of the cuvette 10, which is processed further in a measuring computer 26.

From the picture, the measuring computer 26 determines the outer diameter $d_O$ and the inner diameter $d_I$ in a plurality of rotational positions of the cuvette body 12 and generates a respective average value from the determined diameter values. From the two average values thus determined, a shape correction value F is calculated, depending on the deviation of the former values from an ideal set value, which shape correction value F is included in the later determination of an analyte measuring value in a laboratory analyzer 30. The shape correction value F corrects or standardizes, on the one hand, the influence of the varying length of the radial measuring path 35 inside the cuvette body 12 and, on the other hand, the radiation absorption of the glass material of the cuvette body 12 varying with the wall thickness D.

A barcode is first generated in a virtual manner from the shape correction value F in the measuring computer 26, which is then reproduced by a printer 28. The two-dimensional barcode 22 is adhered to the outside of the cuvette body 12. The reagent 20 is thereafter filled into the cuvette 10 and the cuvette body 12 is closed with the transport closure 18, for example, a screw lid.

The cuvette 10 is shipped to the user. For the quantitative determination of an analyte in a liquid sample, the user removes the transport closure 18 and fills a certain quantity of the liquid, for example, waste water, as a sample 21 into the cuvette 10. The cuvette 10 is thereafter closed again with the transport closure 18, and the reagent 20 is mixed with the sample 21 in the cuvette 10 by shaking.

The cuvette 10 is then inserted into a cuvette chamber 42 of the analyzer 30, whereupon the analysis process starts automatically. At the bottom of the cuvette chamber 42, a rotary disk 36 is arranged which can be driven by an electric drive motor 38. The cuvette 10 is first turned until the barcode reader 32 of the analyzer 30, which is designed as digital camera, has found the barcode 22 on the outer side 14 of the cuvette body 12. The barcode reader 32 thereafter reads out the barcode 22 in the form of a picture, from which, among others, the shape correction value F is then determined in an analyzer control 40.

The absorbance is further determined by means of a photometer 34 comprising, among others, a photometer transmitter $34_1$ and a photometer receiver $34_2$. This is effected at a plurality of rotational positions while the cuvette 10 is turned so that artifacts can be suppressed, should any exist, and a reliable average signal value from the photometer 34 is available. In the analyzer control 40, a measuring value is calculated from the signal value using the shape correction value F, and is outputted optically, acoustically and/or electronically.

The present invention is not limited to embodiments described herein; reference should be had to the appended claims.

What is claimed is:

1. A method for determining a shape correction value for a laboratory liquid-analysis cuvette comprising a cuvette body with an opening side, a bar code and a cross-section for a photometric liquid analysis of a sample in an analyzer,
the analyzer comprising:
    a photometer comprising a photometer transmitter and a photometer receiver which determine a signal value by measuring along a photometric measuring path; and
    an analyzer control;
the method comprising:
    providing a digital camera;
    providing a measuring computer;
    providing a printer;
    providing the laboratory liquid-analysis cuvette;
    optically measuring at least one of an inside diameter and an outside diameter of the cuvette body with the digital camera by taking a picture of the opening side of the cuvette body;
    determining at least one of the inside diameter and the outside diameter of the cuvette body in a plurality of rotational positions with the measuring computer based on the optical measurement;
    generating an average value for at least one of the inside diameter and the outside diameter of the cuvette body with the measuring computer;
    calculating a shape correction value with the measuring computer from the average value, the shape correction value being a value which correlates with a deviation of an exact length of the photometric measuring path inside the cuvette body with an ideal photometric measuring path length;

printing the shape correction value as a two-dimensional barcode for the cuvette body with the printer; and adhering the two-dimensional barcode comprising the shape correction value to the cuvette body, wherein, during the photometric liquid analysis of the sample, the shape correction value is provided to the analyzer control of the analyzer, and the analyzer control calculates an analyte measuring value from the signal value and the shape correction value.

2. The method as recited in claim 1, wherein the analyzer further comprises a barcode reader configured to read the two dimensional barcode.

3. The method as recited in claim 1, wherein the analyzer further comprises a cuvette turning device configured to turn the laboratory liquid-analysis cuvette.

4. The method as recited in claim 1, wherein, after optically measuring at least one of the inside diameter and the outside diameter of the cuvette body to obtain the measured cuvette body diameter, the method further comprises:

filling the laboratory liquid-analysis cuvette with a reagent configured to react in a detectable manner with an analyte in a liquid to be analyzed; and closing the laboratory liquid-analysis cuvette with a transport closure.

5. The method as recited in claim 1, wherein the shape correction value is calculated from both the measured inner diameter and from the measured outer diameter.

6. The method as recited in claim 1, wherein the cross section of the cuvette body is circular.

7. A system for measuring a shape-corrected absorbance of an analyte in a sample, the system comprising:

an analyzer comprising,
   an analyzer control,
   a photometer comprising a photometer transmitter and a photometer receiver configured to measure along a photometric measuring path, and
   a barcode reader configured to read a two dimensional barcode;

a laboratory liquid-analysis cuvette comprising,
   a cuvette body comprising a cross-section and an opening side, the laboratory liquid-analysis cuvette being configured to have a reagent react with the analyte in the sample in a detectable manner when placed therein,
   a two-dimensional barcode adhered to the cuvette body, and
   a shape correction value stored for the cuvette body in the two-dimensional barcode;

a digital camera configured to perform an optical measurement of at least one of an inside diameter and an outside diameter of the cuvette body by taking a picture of the opening side of the cuvette body;

a printer; and a measuring computer configured,
   to generate an average value for at least one of the inside diameter and the outside diameter of the cuvette body based on the optical measurement,
   to calculate the shape correction value from the average value, the shape correction value being a value which correlates with a deviation of an exact length of the photometric measuring path inside the cuvette body with an ideal photometric measuring path length, and
   to store the shape correction value as the two-dimensional barcode for the cuvette body via the printer, wherein, the photometer is configured to measure along the photometric measuring path so as to obtain a first absorbance of the analyte in the sample, and the analyzer control is configured to correct the first absorbance with the shape correction value read by the barcode reader so as to determine the shape-corrected absorbance of the analyte in the sample.

8. The system as recited in claim 7, further comprising:

a cuvette turning device configured to turn the laboratory liquid-analysis cuvette so that a plurality of optical measurements of the inside diameter or of the outside diameter of the cuvette body is performed by the digital camera, wherein, the shape correction value is calculated based on the plurality of optical measurements.

9. The system as recited in claim 7, wherein, the digital camera is configured to perform an optical measurement of the inside diameter of the cuvette body to obtain a measured inside diameter, and an optical measurement of the outside diameter of the cuvette body to obtain a measured outside diameter, and the shape correction value is calculated from both the measured inner diameter and from the measured outer diameter.

10. The system as recited in claim 7, wherein the cross section of the cuvette body is circular.

* * * * *